US00PP31701P2

(12) United States Plant Patent
Bradford et al.

(10) Patent No.: US PP31,701 P2
(45) Date of Patent: Apr. 28, 2020

(54) PEACH TREE NAMED 'RED PRINCESS VI'

(50) Latin Name: *Prunus persica*
Varietal Denomination: RED PRINCESS VI

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/501,443

(22) Filed: Apr. 17, 2019

(51) Int. Cl.
*A01H 5/08* (2018.01)
*A01H 6/74* (2018.01)

(52) U.S. Cl.
USPC ..... Plt./197
CPC ..... *A01H 6/7463* (2018.05)

(58) Field of Classification Search
USPC ..... Plt./197
CPC ..... A01H 6/7463
See application file for complete search history.

(56) References Cited

U.S. PATENT DOCUMENTS

| | | | |
|---|---|---|---|
| PP15,143 | P2 | 9/2004 | Bradford |
| PP25,793 | P3 | 8/2015 | Bradford |
| PP28,996 | P2 | 2/2018 | Bradford |

*Primary Examiner* — Anne Marie Grunberg

(57) ABSTRACT

The present invention relates to a new and distinct variety of peach tree, *Prunus persica*, broadly characterized by a large size, vigorous, hardy, self-fertile, productive and regular bearing tree. The variety blooms during the late blooming season and requires about 700 chilling hours. The fruit matures under the ecological conditions described in mid to late August with the first picking on Aug. 21, 2018. The fruit is uniform, large in size, globose in shape, clingstone in type, firm in texture, mostly yellow in flesh color, mostly red and orange in skin color, and traditional peach in flavor.

1 Drawing Sheet

Botanical classification: *Prunus persica.*
Variety denomination: 'RED PRINCESS VI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'RED PRINCESS VI'.

The present variety was hybridized by us in 2008 as a first generation cross using 'July Princess' (U.S. Plant Pat. No. 28,996) peach as the selected seed parent and 'August Bright' (U.S. Plant Pat. No. 15,143) nectarine as the selected pollenparent. Upon reaching maturity the fruit from this cross was harvested, and the seeds were removed, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2013 we selected the present variety as a single tree from the group of seedlings described above. Subsequent to origination of the present variety of peach tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its seed parent, 'July Princess' (U.S. Plant Pat. No. 28,996) peach by having a large and vigorous tree, by being self-fertile, and by producing peaches that mostly red to orange in skin color, and yellow in flesh color, but is quite distinguished therefrom by blooming later, by requiring more chilling, and by producing peaches that are clingstone instead of freestone in type, that are larger in size, and that mature about thirty days later.

The present variety is similar to its pollen parent, 'August Bright' (U.S. Plant Pat. No. 15,143) nectarine, by having a medium to large tree, by being self-fertile, and by producing fruit that is mostly red to orange in skin color, yellow in flesh color, fairly globose in shape, clingstone in type and firm in texture, but is quite distinguished therefrom by having large showy instead of small non-showy blossoms and by producing peaches instead of nectarines that mature about eight days later and have a bitter instead of sweet kernel.

The present variety is most similar to 'Summer Princess' peach (U.S. Plant Pat. No. 25,793) by having large blossoms, by being self-fertile, and by producing peaches that are mostly red to orange in skin color, mostly yellow in flesh color, large in size, clingstone in type, globose in shape, and firm in texture, but is distinguished therefrom by requiring more chilling hours, by having reniform instead of globose leaf glands, and by producing fruit that is somewhat sweeter and that matures about twenty days earlier. It is to be noted that 'Summer Princess' was originally claimed to ripen the last week of August, but has since been determined to ripen the second week of September in commercial orchard conditions.

SUMMARY OF VARIETY

In summary, the present peach variety is characterized by a large size, vigorous, hardy, self-fertile, productive and regular bearing tree. The variety blooms during the late blooming season and requires about 700 chilling hours. The fruit matures under the ecological conditions described in mid to late August with the first picking on Aug. 21, 2018. The fruit is uniform, large in size, globose in shape, clingstone in type, firm in texture, mostly yellow in flesh color, mostly red and orange in skin color, and traditional peach in flavor.

DRAWING

The accompanying photograph consists of four whole fruits positioned to display the characteristics of the skin color and form, one divided fruit to reveal the flesh and stone, a tip shoot of new leaf growth, typical leaves, and two insets depicting the flower buds and blossoms as they appeared on the tree during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Aug. 23, 2018, on the original tree during its tenth growing season. The blossom and flower descriptions were made the previous blooming season. All major color code designations are by reference to the Inter-Society Color Council, National Bureau of Standards. Common color names are also used occasionally.

PARENTAGE

Seed parent: 'July Princess' (U.S. Plant Pat. No. 28,996) peach.

Pollen parent: 'August Bright' (U.S. Plant Pat. No. 15,143) nectarine.

TREE

Size: Large, reaching and maintaining a height of 14' [4.27 m.] and a spread of 12' [3.66 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 700 hours.

Trunk:

*Size*.—Medium, reaching a maximum diameter of 5" [127 mm.] after the tenth growing season.

*Texture*.—Medium, shaggy.

*Bark color*.—A Grayish yellowish brown [80. gy.yBr] and Moderate yellowish brown [77. m.yBr] variegation with Dark yellowish brown [78. d.yBr] crevices present.

*Lenticels*.—Approximate Number Per Square Inch: 7. Color: Strong brown [55. s.Br]. Average Size: ⅛" [3.2 mm.] in length. The width is typically one fourth as much as the length. Shape: Eye-shaped.

Branches:

*Size*.—Medium, diameter of main scaffold is 2¾" [69.9 mm.] measured 12" above the crotch, diameter of limb is 1¾" [44.5 mm.] measured 12" above the first fork.

*Texture*.—Fairly smooth on first and second year wood, increasing roughness with age.

*Color*.—1st Year Wood Topside: Grayish red [19. gy.R]. 1st Year Wood Underside: Brilliant yellow green [116. brill.YG]. Older Wood: A Light grayish brown [60. l.gy.Br] and Strong brown [55. s.Br] variegation.

*Lenticels*.—Number Per Square Inch: About 65 on second year wood. Color: Light yellowish brown [76. l.yBr]. Average Size: Medium, 1/16" [1.6 mm.] in length. The width is typically one fourth as much as the length. Shape: Eye-shaped.

Leaves:

*Size*.—Large. Average Length: 6⅝" [168.3 mm.]. Average Width: 1¾" [44.5 mm.].

*Arrangement*.—Alternate.

*Thickness*.—Medium.

*Form*.—Elliptical.

*Apex*.—Acuminate.

*Base*.—Acute, average angle of 45 degrees.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Vein color*.—Light greenish yellow [101. l.gY].

*Petiole*.—Average Length: ½" [12.7 mm.]. Average Thickness: 1/16" [1.6 mm.]. Color: Strong yellow green [117. s.YG].

*Stipules*.—Number: Usually 2 per leaf, up to 6 per growing tip. Average Length: ¼" [6.4 mm.]. Color: Vivid yellow green [115. v.YG] becoming Dark olive brown [96. d.OlBr] with age.

*Glands*.—Number: 2 to 4 per leaf. Position: Alternate positioned near the intersection of petiole and base of blade. Form: Reniform. Size: Medium, about 1/48" [0.5 mm.] in diameter. Color: Moderate olive green [125. m.OlG] acquiring a Dark olive brown [96. d.OlBr] center with age.

*Leaf buds*.—Pointed.

Flower buds:

*Hardiness*.—Hardy, with respect to central California blooming season.

*Diameter*.—Typically ⅜" [9.5 mm.] 1 week before bloom.

*Length*.—Typically ⅝" [15.9 mm.] 1 week before bloom.

*Form*.—Free, not touching.

*Surface*.—Pubescent.

*Tip color*.—Light pink [4. l.Pk].

Flowers: Perfect, complete, perigynous, usually a single pistil, about thirty stamens, five sepal and petal locations alternately positioned.

*Type*.—Showy, large.

*Average flower diameter*.—1 15/16" [49.2 mm.].

*Average flower depth*.—7/16" [11.1 mm.] when fully open.

*Number of petals*.—Usually five, extra petal fragments occur occasionally, double blossoms rarely observed.

*Petal arrangement*.—Overlapping.

*Petal shape*.—Circular to oval.

*Petal margin*.—Entire, wavy.

*Average petal diameter*.—9/16" [14.3 mm.].

*Average petal length*.—5/8" [15.9 mm.].

*Petal apex*.—Rounded.

*Petal base*.—Rounded to somewhat truncate.

*Petal color*.—Pale pink [7. p.Pk] toward the apex, Moderate pink [5. m.Pk] toward the base on both sides.

*Anther color*.—Strong red [12. s.R] over a Brilliant yellow [83. brill.Y] center at bloom onset.

*Pollen*.—Anthers produce an abundance of Brilliant yellow [83. brill.Y] pollen.

*Stigma color*.—Light greenish yellow [101. l.gY].

*Stigma position*.—Typically located about even with the nearby anthers.

*Stamen position*.—Typically located about 3/64" [1.2 mm] below the petals.

*Average pistil length*.—5/8" [15.9 mm.].

*Average stamen length*.—9/16" [14.3 mm.].

*Ovary*.—Pubescent.

*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.

*Sepal length*.—5/16" [7.9 mm.].

*Sepal width*.—1/4" [6.4 mm.].

*Sepal apex*.—Rounded to obtuse to match the sepal length and width.

*Sepal margin*.—Fairly smooth.

*Fragrance*.—Moderate.

*Blooming period*.—Late, four days after 'Summer Princess' (U.S. Plant Pat. No. 25,793) peach.

*Onset of bloom*.—One percent on Mar. 7, 2018.

*Date of full bloom*.—Mar. 17, 2018.

*Duration of bloom*.—One to two weeks, dependent on ambient temperature.

*Bloom density*.—Medium.

*Number per cluster*.—1 to 3 with single flowers most common.

FRUIT

Maturity when described: Firm ripe, Aug. 23, 2018.

Date of first picking: Aug. 21, 2018.

Date of last picking: Sep. 1, 2018.

Size: Uniform, large.

*Average diameter axially*.—3 5/8" [92.1 mm.].

*Average diameter across suture plane*.—3 5/8" [92.1 mm.].

*Average diameter across cheek plane*.—3 5/8" [92.1 mm.].

*Typical weight*.—13.0 ounces [369 grams].

Form: Mostly uniform, globose.

*Longitudinal section form*.—Round.

*Axial view*.—Round.

Suture: A distinct Dark reddish orange [38. d.rO] line located in a medium to deep groove that extends from the base to just beyond the pistil point, with a slight depression beyond the pistil point.

*Near the base*.—A sharp groove.

*Along the side*.—A shallow trough.

*Near the apex*.—A shallow groove.

Ventral surface: Rounded slightly, lipped stronger on one side.

Lips: Unequal.

Cavity: Flaring, narrow, elongated in the suture plane.

*Depth*.—1/2" [12.7 mm.].

*Breadth*.—7/8" [22.2 mm.].

Base: Truncate.

Apex: Rounded to slightly truncate.

Pistil point: Apical, typically 1/16" [1.6 mm.] in length, usually depressed within the suture.

Stem: Medium to large.

*Average length*.—7/16" [11.1 mm.].

*Average width*.—3/16" [4.8 mm.].

Skin:

*Thickness*.—Medium.

*Surface*.—Pubescent.

*Tenacity*.—Tenacious to flesh.

*Astringency*.—Astringent.

*Tendency to crack*.—None observed.

*Color*.—Dark red [16. d.R] over a Strong orange [50. s.O] background with some Brilliant yellow [83. brill.Y] areas if sun protected.

*Down*.—Very short, does not roll up when rubbed.

Flesh:

*Color*.—Vivid yellow [82. v.Y] with Dark red [16. d.R] bleeding near the stone and Moderate red [15. m.R] flecking throughout.

*Surface of pit cavity*.—Covered with Deep red [13. deep R] broken fibers when twisted away from the stone.

*Amygdalin*.—Moderate.

*Juice*.—Abundant, rich.

*Texture*.—Firm, genetically non-melting.

*Ripens*.—Fairly evenly.

*Flavor*.—Traditional peach flavor, moderately acidic, sweet, typically 15-16 brix.

*Aroma*.—Moderate.

*Eating quality*.—Very good.

STONE

Type: Clingstone.

Form: Oval to obovate.

Hilum: Narrow.

Base: Rounded to truncate.

Apex: Acute with a 1/16" [1.6 mm.] tip.

Sides: Slightly unequal.

Surface: Irregularly furrowed toward the apex, pitted toward the base.

Ridges: Rounded.

External color: Dark reddish brown [44. d.rBr].

Pit wall color when cracked: Grayish reddish brown [46. gy.rBr].
Cavity surface color: A mix of Light brown [57. l.Br] and Moderate brown [58. m.Br].
Average pit wall thickness: 5/16" [7.9 mm.].
Average length: 1½" [38.1 mm.].
Average width: 1 3/16" [30.2 mm.].
Average breadth: 15/16" [23.8 mm.].
Tendency to split: None observed.
Kernel:
*Form*.—Oval.
*Skin color*.—Moderate orange yellow [71. m.OY].
*Pellicle color*.—Dark yellowish brown [78. d.yBr].
*Vein color*.—Deep orange yellow [69. deep OY].
*Taste*.—Bitter.
*Viable*.—Yes.
*Average width*.—½" [12.7 mm.].
*Average length*.—¾" [19.1 mm.].
*Amygdalin*.—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'Summer Princess' peach (U.S. Plant Pat. No. 25,793) by having large blossoms, by being self-fertile, and by producing peaches that are mostly red to orange in skin color, mostly yellow in flesh color, large in size, clingstone in type, globose in shape, and firm in texture, but is distinguished therefrom by requiring more chilling hours, by having reniform instead of globose leaf glands, and by producing fruit that is somewhat sweeter and that matures about twenty days earlier.

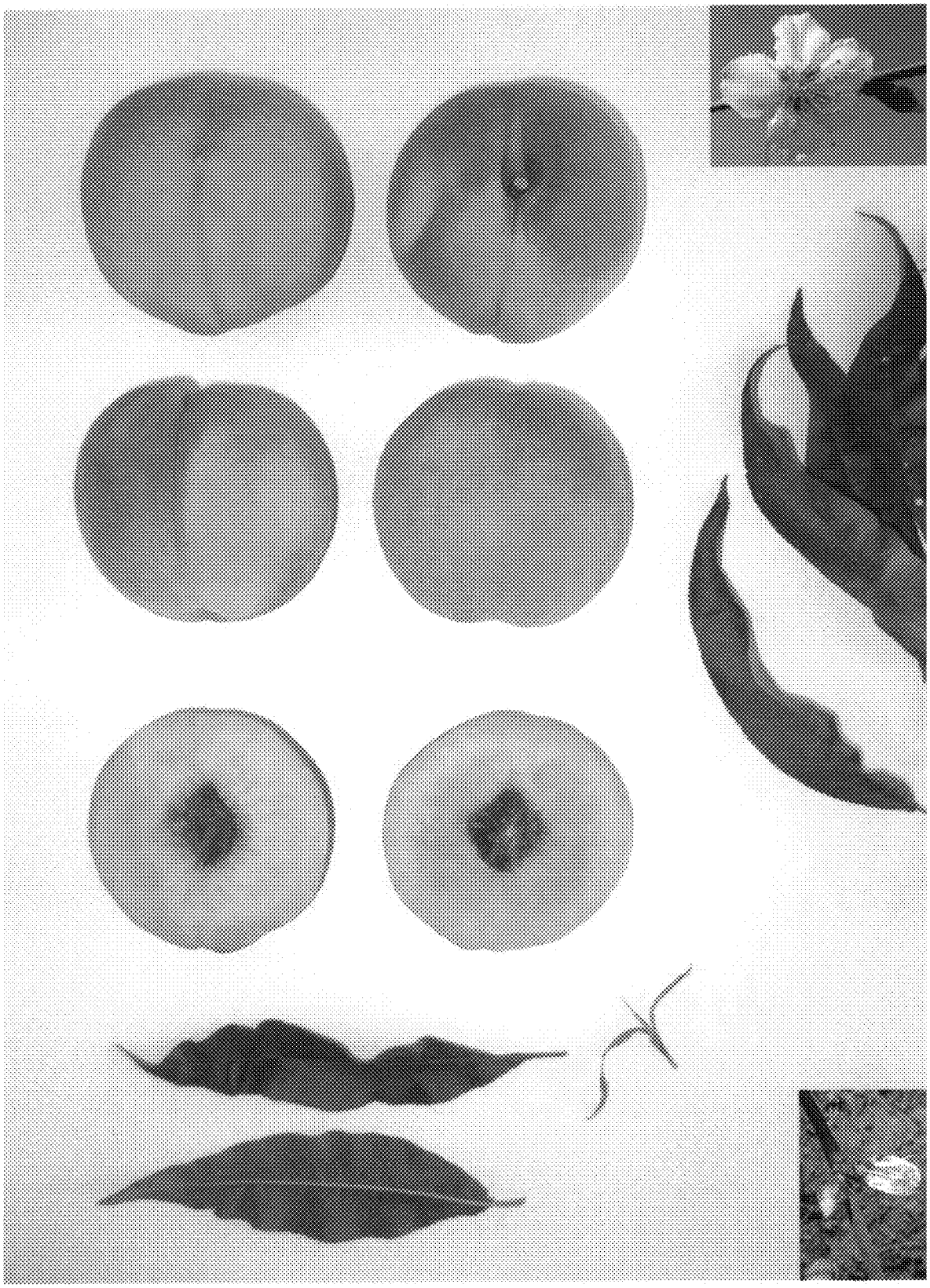

* * * * *